United States Patent [19]

Schave et al.

[11] Patent Number: 4,585,343

[45] Date of Patent: Apr. 29, 1986

[54] APPARATUS AND METHOD FOR INSPECTING GLASS

[75] Inventors: Richard D. Schave, Perrysburg; Walter D. McComb, Oregon; Andrew W. Rudolph, Elmore, all of Ohio

[73] Assignee: Libbey-Owens-Ford Company, Toledo, Ohio

[21] Appl. No.: 548,684

[22] Filed: Nov. 4, 1983

[51] Int. Cl.$^4$ .................. G01N 21/55; G01N 21/89; G01B 11/30

[52] U.S. Cl. ........................... 356/237; 65/29; 356/371; 356/430; 356/445

[58] Field of Search .............. 356/237, 445, 371, 376, 356/430, 431; 364/473; 65/29, 162; 358/101, 106

[56] References Cited

U.S. PATENT DOCUMENTS

| | | | |
|---|---|---|---|
| 3,779,731 | 12/1973 | Pollock et al. | 364/473 X |
| 3,857,637 | 12/1974 | Obenreder | 356/237 X |
| 4,139,306 | 2/1979 | Norton | 356/430 X |
| 4,223,346 | 9/1980 | Neiheisel et al. | 356/237 X |
| 4,403,294 | 9/1983 | Hamada et al. | 356/237 X |

*Primary Examiner*—Vincent P. McGraw
*Assistant Examiner*—Robert D. V. Thompson, III
*Attorney, Agent, or Firm*—Phillip S. Oberlin

[57] ABSTRACT

The present invention relates to an inspection apparatus for detecting the surface distortion in a sheet of material such as a sheet of glass, for example, and for indicating whether the level of distortion detected in the inspected sheet is unacceptable. The inspection apparatus includes a light source mounted to direct a first beam of light toward one surface of the sheet at an oblique angle of incidence to cause a second beam of light to be reflected therefrom. A light detector is mounted to receive the reflected beam and is responsive to a light pattern produced by the reflected beam of light for generating an output signal representing the width of the light pattern. The width of the light pattern is a function of the surface distortion of the portion of the surface from which the beam is reflected. A control circuit is responsive to the detector output signals for generating an actual distortion signal representing the amount of surface distortion in the inspected portion of the surface. In the preferred embodiment of the invention, a plurality of individual actual distortion signals are generated and are utilized by the control circuit for generating an overall distortion signal representing the overall distortion in the inspected sheet. The overall distortion signal is compared with a reference distortion signal which defines the acceptable level of surface distortion. Based on the comparison, an indicator is provided for indicating whether the inspected sheet is unacceptable.

10 Claims, 5 Drawing Figures

4,585,343

APPARATUS AND METHOD FOR INSPECTING GLASS

BACKGROUND OF THE INVENTION

The present invention relates generally to an inspection apparatus for detecting surface distortion in a sheet of material, such as a glass plate, for example. More particularly, the present invention concerns an apparatus for determining the amount of surface distortion in a glass plate as the glass is carried past the inspection apparatus.

In the known methods of making and shaping glass, defects may inadvertently be produced in the glass which render the glass optically imperfect. Defects may also be produced in the glass during subsequent manufacturing operations such as during a tempering operation, for example. Among the optical imperfections that may be produced is surface distortion. Surface distortion, as the term is used herein, generally refers to variations in surface flatness, i.e. concave and convex portions.

Surface distortion in glass causes the glass surface to reflect a distorted image. For example, convex portions shrink the image and concave portions magnify the image. When excessive distortion is present, the distorted images detract from the architectural beauty and are therefore not desirable.

In addition to other methods, one approach which has been proposed for detecting surface distortion of a piece of glass is disclosed in U.S. Pat. No. 3,857,637 to Obenreder. The Obenreder patent discloses an inspection apparatus which utilizes a light source and a position sensing photodetector for detecting concave and convex portions on the inspected surface and the amplitude of such portions. The light source, such as a continuous laser, directs a beam of light on the upper surface of a glass plate traveling at a constant speed along a predetermined path relative to the light source. The position sensing photodetector is mounted to detect the portion of the light beam reflected by the upper inspected surface of the glass plate.

If the inspected surface is flat, the reflected portion of the beam will be received by the photodetector along a predetermined reference line. When the light beam is reflected from concave or convex portions in the surface, the reflected beam will be displaced from this reference line. The inspection apparatus includes means responsive to the detector output signals to produce a surface flatness profile showing the nature of the surface curvature, i.e. concave or convex, and the amplitude of the curvature. While such an apparatus is capable of determining the surface flatness of a sheet of glass, there is no means provided for analyzing the data for determining whether the distortion level of an inspected sheet of glass is unacceptable. Also, such an apparatus is subject to errors from changes in glass position during the measurement process.

SUMMARY OF THE INVENTION

The present invention concerns an inspection apparatus for detecting surface distortion such as roll corrugation in a sheet of material such as a glass plate, for example, and for indicating whether the level of distortion in the inspected sheet is greater than a predetermined amount. The apparatus includes a light source mounted to direct a first beam of light toward one surface of the sheet at an oblique angle of incidence to cause a second beam of light to be reflected therefrom. A light detector means is mounted to receive the reflected beam and is responsive to a light pattern on the detector means produced from the reflected beam of light for generating an output signal representing the width of the light pattern. The width of the light pattern is a function of the surface distortion of the portion of the surface from which the beam is reflected.

The light pattern received by the detector means will have a predetermined reference width when the second beam is reflected from a substantially flat portion of the inspected surface. The difference in width of the light pattern sensed by the detector means relative to the width of the light pattern produced by flat glass represents a variation in the surface flatness of the inspected sheet of glass. For example, in the preferred embodiment of the invention, increases in width of the light pattern represent a detection of a concave portion on the surface, while decreases in width of the image represent an indication of a convex portion. A control means is responsive to the detector output signal for generating an actual distortion signal representing the amount of surface distortion in the inspected portion of the surface.

Since the inspection apparatus detects distortion by measuring the width of a light pattern formed by the diode array, rather than by detecting the exact position at which the reflected light beam falls on the diode array, as disclosed in the above-discussed U.S. Pat. No. 3,857,637 to Obenreder, the inspection apparatus is less sensitive to variations in the position of the inspected glass plate as compared with the prior art systems.

In the preferred embodiment of the invention, a plurality of actual distortion signals are generated, each representing the distortion in a separate one of a plurality of inspected portions of the glass. The control means is responsive to the plurality of actual distortion signals for generating an overall distortion signal representative of the distortion in the entire sheet. The control means stores a predetermined reference distortion signal which defines an acceptable level of surface distortion and is responsive to the overall distortion signal and the reference distortion signal for indicating whether the amount of overall distortion exceeds the predetermined level. The present invention can include a display means for displaying the value of the overall distortion signal to an operator. Also, a strip chart recorder can be provided for recording a flatness profile of the inspected sheet.

In addition to providing an indication of the distortion of the inspected sheets, the inspection apparatus can also be utilized to provide other control functions. For example, in glass tempering operations, the amount of distortion introduced by the tempering operation is a function of the temperature maintained in the tempering furnace. Thus, if the inspection apparatus is utilized in a tempering system, the apparatus can be connected to control the furnace temperature in order to reduce any detected distortion.

BRIEF DESCRIPTION OF THE DRAWINGS

The above, as well as other advantages of the present invention, will become readily apparent to one skilled in the art from reading the following detailed description in conjunction with the attached drawings in which.

DESCRIPTION OF THE PREFERRED EMBODIMENT

Figure 1:
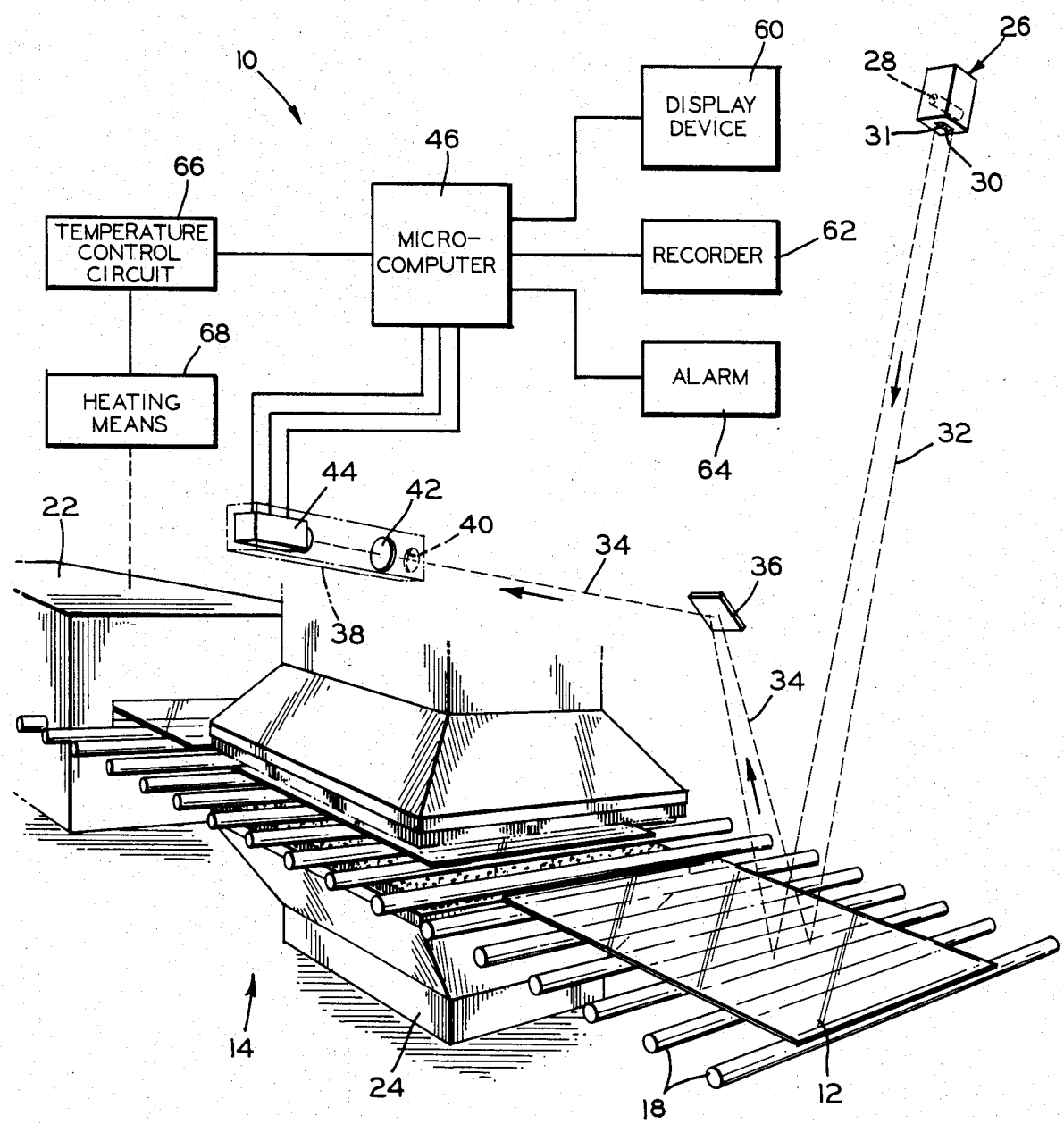
FIG. 1 is a combined perspective view and block diagram illustrating the inspection apparatus of the present invention in conjunction with a glass heat treating system.

Referring to FIG. 1, there is shown a combined perspective view and block diagram illustrating an inspection apparatus 10 of the present invention for use in inspecting individual sheets of glass 12 which have been treated by a glass tempering system 14. It should be noted at the outset of this description that, while the present invention is described as an apparatus for inspecting glass, the apparatus can be utilized in other applications wherein it is desired to inspect a reflective surface of an article for surface distortion.

In FIG. 1, the glass tempering system 14 includes a plurality of conveyor rollers 18 for conveying the individual glass sheets 12 through the system. The rollers 18 are typically coupled to a conveyor drive means (not shown) capable of suitably driving the rollers 18. The conveyor rollers 18 support the individual glass sheets 12 as they are conveyed through a tempering furnace 22 and a cooling or quenching station 24.

Generally, there are three types of surface distortion which can be caused by a glass tempering operation. These include (1) edge deformation wherein the edge portions of a tempered sheet do not remain flat with the central portion of the sheet, (2) roll corrugation wherein a series of alternating convex and concave portions are formed along the glass sheet, and (3) bow deformation wherein the glass sheet may be bowed either upwardly or downwardly. Since each of the above three types of distortion can result in an optically imperfect sheet of glass, the tempering operation must be carefully monitored to minimize these types of distortion. The inspecting apparatus of the present invention is specifically designed to detect the above described types of surface distortion.

As an individual sheet 12 of glass exits the quenching station 24, the glass is inspected by the apparatus 10. The apparatus 10 includes a light source 26 having a lamp 28, a "milk glass" diffuser 30 to provide a beam of substantially uniform light intensity, and a slit 31 to shape the diffused light into the desired shape for effectively directing a light beam 32 at an oblique angle onto the glass sheet 12. Typically, the slit 31 is generally rectangular in shape and the light source 26 is oriented such that the longer dimension of the slit 31 is disposed perpendicularly to the linear path of the glass sheet 12.

A portion of the beam 32 is reflected upwardly by the glass sheet 12 as a reflected beam 34. In instances wherein the glass sheet 12 is relatively transparent, the beam 32 is reflected by both the upper and lower surfaces of the glass sheet 12. A flat mirror 36 is positioned in the path of the reflected beam 34 and is adapted to direct the reflected beam 34 toward a light detector means such as a camera assembly 38. The camera assembly 38 includes an adjustable aperture 40 and a lens 42 for producing an image in a camera unit 44. The camera unit 44 comprises an array of photosensitive devices such as photodiodes which, as will be discussed, are utilized to determine the width of the light pattern produced on the diode array by the reflected beam 34.

The dimensions of the slit 31 of the light source 26, and the relative position between the camera assembly 38 and the glass sheet 12 are selected such that, when the portion of the surface of the glass sheet 12 which reflects the beam 32 is flat and contains no distortion, the image produced in camera unit 44 will have predetermined reference dimensions. It has been found that a slit 31 of 1 inch across and $5\frac{3}{4}$ inches in length used with a 500 watt quartz iodine lamp provides a suitable light source, while a conventional Reticon camera provides a suitable camera assembly.

The manner in which the camera assembly 38 is utilized to detect variations in the surface flatness of the glass sheet 12 will now be discussed. Basically, the system functions to measure the amount of surface distortion in a sheet of material by directing a light beam onto the surface to be inspected, and subsequently determining the width of a light pattern formed on the camera diode array by the reflected portion of the light beam. The width of the light pattern is a function of the amount of surface distortion in the inspected area of glass. When the glass is relatively flat and contains no distortion, the light pattern on the diode array of the camera unit 44 will have a predetermined width. However, as surface distortion is detected, the width of the light pattern as sensed by the camera diode array will vary. These variations in width of the light pattern can be utilized to determine the amount of surface distortion in the inspected glass.

Figure 2:
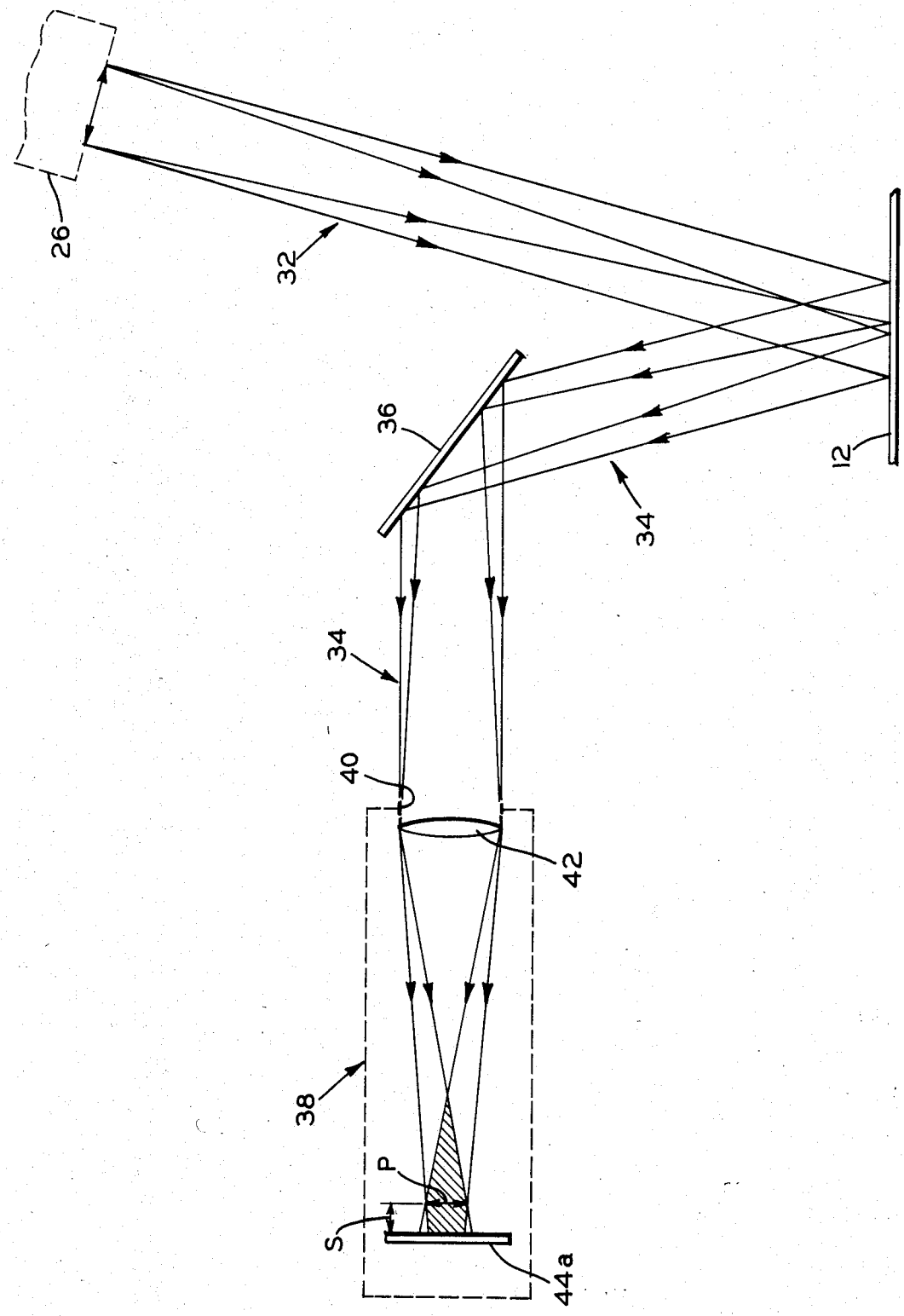
FIG. 2 is a schematic diagram illustrating the manner in which an image is formed by the reflected beam in the camera assembly and is focused in a plane located in front of the camera diode array.

Referring to FIG. 2, the light beam 32 is directed downwardly onto the surface of the glass sheet 12 and is reflected upwardly toward the flat mirror 36. The flat mirror 36 directs the reflected beam 34 through the camera aperture 40, and the camera lens 42 causes an image to be focused in a plane P offset from a camera diode array 44a by a distance S. As surface distortion is detected, the distance the image plane is spaced from the diode array 44a varies to cause the width of the light pattern as seen by the diode array 44a to vary. As will be discussed, such variations in width of the light pattern are a function of the surface distortion in the inspected glass.

Figure 3A:
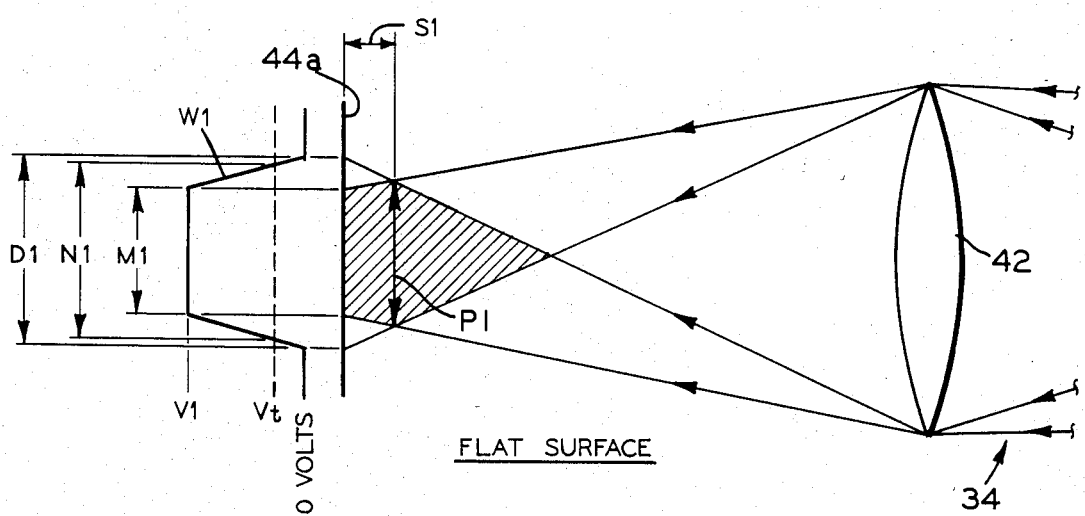
FIGS. 3a through 3c are schematic diagrams illustrating the manner in which variations in surface flatness of an inspected sheet of glass causes the spacing between the plane in which the image is focused and the diode array to vary, thus causing the width of the light pattern as seen by the diode array to vary.
Figure 3B:
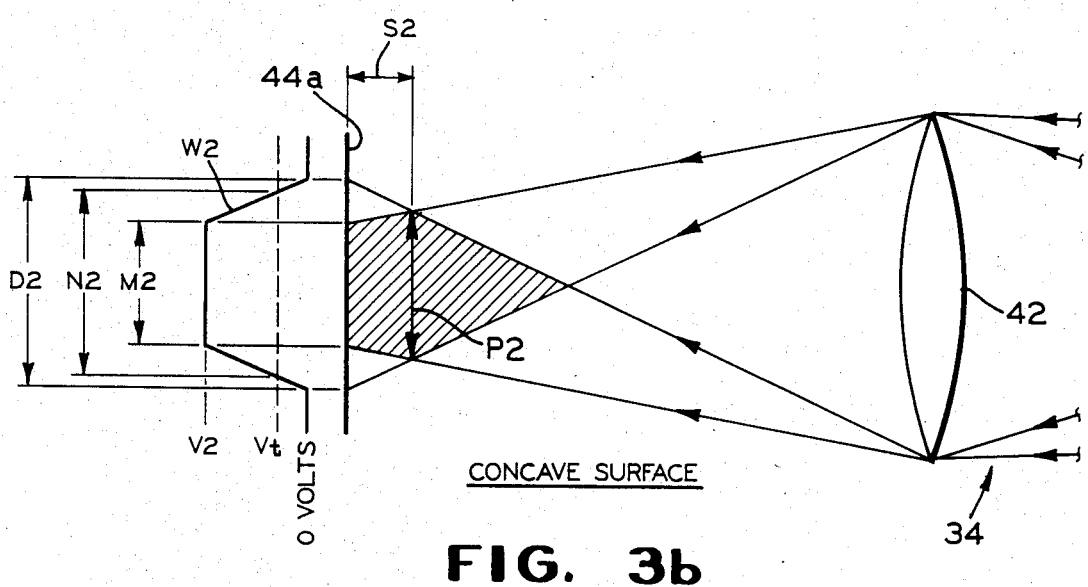
Figure 3C:
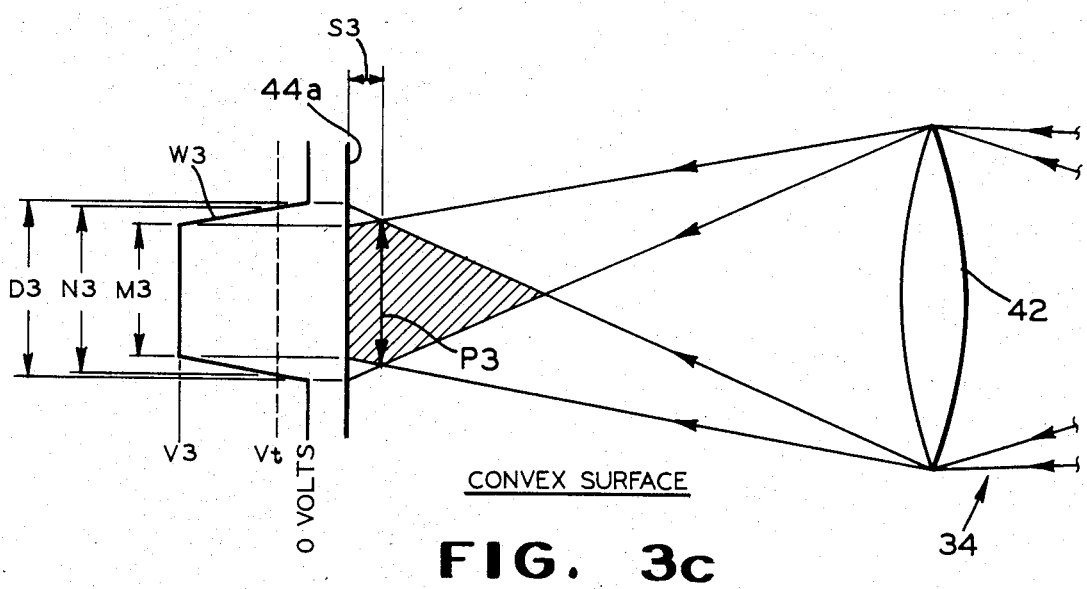

Referring to FIGS. 3a through 3c, there is shown the manner in which the spacing between the diode array 44a and the plane in which the image is focused varies as surface distortion is detected in the glass sheet, thus causing the width of the light pattern as seen by the camera diode array 44a to vary. In FIG. 3a, which illustrates the position of an image formed by a beam reflected from a relatively flat portion of the glass sheet, the image is focused in a plane P1 which is spaced a distance S1 from the diode array 44a. As shown in FIG. 3b, when the beam is reflected from a concave portion of the glass sheet, the image is focused in a plane P2 spaced a distance S2 from the diode array 44a which is greater than the distance S1 of FIG. 3a. As shown in FIG. 3c, when the beam is reflected from a convex portion of the glass sheet, the image is focused in a plane P3 spaced a distance S3 from the diode array 44a which is less than the distance S1 of FIG. 3a.

The camera unit 44 functions to generate electrical waveform signals, similar to waveforms W1 through W3 located along the left hand portions of FIGS. 3a through 3c, which represent the intensity and width of the light pattern formed on the diode array 44a by the reflected beam. The magnitude of each portion of the waveforms is a function of the intensity of the light pattern incident on the respective portion of the diode array. In FIGS. 2 and 3a through 3c, the shaded portion represents the portion of the beam wherein a plane parallel to the image plane will have an area of relatively uniform light intensity. In FIGS. 3a through 3c, since the camera diode array 44a is not located along the plane in which the image is focused, the light pattern formed on the diode array 44a is out of focus and is blurred around the periphery of the pattern. The inclined edge portions of the waveforms W1 through W3 represent the blurred portions of respective light pattern.

In order to determine a diode count representative of the width of the light pattern seen by the diode array 44a, those diodes which generate a signal above a predetermined threshold voltage level Vt can be counted. In FIG. 3a, the waveform W1 consists of a portion at a uniform voltage level V1 having a width M1 and inclined portions which decrease to zero volts at a width D1. The number of diodes which generate a signal above the threshold voltage Vt is represented by width N1. Thus, N1 represents the diode count obtained when the beam is reflected from a relatively flat portion of the glass surface. In FIG. 3b, the waveform W2 consists of a portion at a uniform voltage level V2 having a width M2 and inclined portions which decrease to zero volts at a width D2. In this case, the diode count obtained is represented by width N2. In FIG. 3c, the waveform W3 includes a portion of width M3 having a uniform voltage level V3 and inclined portions which decrease to zero volts at a width D3. The diode count in FIG. 3c is represented by width N3.

The distortion value for an inspected portion of glass can be calculated by determining the difference between the diode count obtained for the inspected portion and the diode count representing a flat portion of the sheet of glass. As the image moves away from the diode array, as is the case in FIG. 3b for concave surface distortion, the width of the light pattern on the diode array 44a becomes wider, causing more diodes to be illuminated and increasing the diode count as compared to the flat glass diode count. The distortion value associated with the light pattern produced in FIG. 3b is calculated by subtracting the flat glass diode count N1 of FIG. 3a from the diode count N2 of FIG. 3b. As the image moves toward the diode array, as shown in FIG. 3c for convex surface distortion, the width of the light pattern on the diode array 44a is decreased, thus decreasing the diode count as compared to the flat glass diode count. The distortion value associated with the light pattern produced in FIG. 3c is determined by subtracting the flat glass diode count N1 from the diode count N3 of FIG. 3c. Thus, in the embodiment shown in the drawings, a positive distortion value indicates a detection of a concave surface, while a negative distortion value indicates a detection of a convex surface.

Referring again to FIG. 1, the reflected beam 34 is sensed by the camera unit 44 which, in turn, generates an output signal which is a function of the width of the light pattern produced in the camera unit 44. The output signal generated by the camera unit 44 is supplied to a microcomputer 46. The microcomputer 46 periodically samples the output signal of the camera unit 44 and determines an individual distortion value for the inspected portion of the glass sheet by subtracting the flat glass diode count from the diode count obtained from the inspected portion. After the individual distortion values for an entire glass sheet have been calculated, the microcomputer 46 processes the data to determine an actual overall distortion value representative of the overall distortion in the glass sheet being inspected.

While the actual overall distortion value can be determined in a number of ways, one method which has been used is to compute the average of a predetermined number of the maximum individual distortion values obtained for the inspected sheet. The actual overall distortion value can then be compared to a previously programmed reference distortion value which defines an acceptable level of distortion. Based on the result of the comparison, the microcomputer can provide the operator with an indication as to whether the inspected sheet is acceptable.

The microcomputer 46 is connected to a display device 60 which can be located at an inspection station (not shown) to display the results of current and previous microcomputer distortion value computations. The microcomputer 46 can also be connected to a conventional strip chart recorder 62 which records a profile representing the flatness of the inspected sheet. An alarm 64 can be connected to receive an actuation signal from the microcomputer 46 to alert an operator in the event a particular sheet of glass has been determined to be unacceptable.

Also, in order to obtain an accurate distortion value for an inspected portion of a sheet of glass, it is necessary that the entire light pattern fall on the camera diode array. The microcomputer 46 can monitor the output signal from the camera 44 to determine whether the entire light pattern falls on the diode array 44a. If the entire light pattern is not on the diode array, the microcomputer can generate a signal to inform the operator of this condition.

In addition to providing an indication of the distortion of the inspected sheets, the inspection apparatus can also be utilized to provide further control functions. For example, in glass tempering operations, the amount of distortion introduced by the tempering operation is a function of the temperature at which the tempering furnaces are maintained. Thus, if the inspection apparatus is utilized in a tempering system, the apparatus can be connected to control the furnace temperature in order to reduce any detected distortion. For example, in FIG. 1, the microcomputer 46 is connected to a temperature control circuit 66 which generates a control signal to a heating means 68. In the event the inspection apparatus detects a predetermined number of unacceptable glass sheets, the temperature of the tempering furnace can be decreased to reduce the surface distortion of the sheets.

It should be noted that, while the inspection apparatus has been described for use in detecting distortion in a relatively flat surface of a reflective material, it will be appreciated that the inspection apparatus can also be adapted to detect distortion in a curved sheet of material. In these instances, the apparatus is programmed to compare the width of the light pattern produced by the reflected beam with a predetermined width representing the desired curvature of the inspected portion of the sheet.

In accordance with the provisions of the patent statutes, the principles and mode of operation of the present invention have been discussed in what is considered to represent its best embodiment. However, it should be understood that the invention may be practiced otherwise than as specifically illustrated and described without departing from its spirit or scope.

What is claimed is:

1. An inspection apparatus for detecting surface distortion in a sheet of reflective material comprising:
a light source mounted to direct a first beam of light having a predetermined width toward a portion of the sheet at an oblique angle of incidence to cause a second beam of light to be reflected therefrom;
light detector means mounted to receive a light pattern produced by the second reflected beam for generating an output signal representing the width of said light pattern, said light pattern having a width which is a function of both the width of the first beam and the surface distortion of the portion of the surface from which the second beam is reflected; and
means responsive to the detector output signal for generating an actual distortion signal representing the amount of surface distortion in the inspected portion of the sheet.

2. The inspection apparatus according to claim 1 wherein said light detector means generates a plurality of detector output signals, each of said output signals representing the width of a light pattern produced by the reflection of said incident beam from a separate inspected portion of the sheet, means responsive to each of said detector output signals for generating an actual distortion signal representative of the distortion in the respective inspected portions of the sheet, and means responsive to said actual distortion signals for generating an overall distortion signal representative of the distortion in the entire sheet.

3. The inspection apparatus according to claim 2 including means for storing a predetermined reference distortion signal defining a predetermined level of surface distortion, and means responsive to said overall distortion signal and said reference distortion signal for indicating when the amount of overall distortion exceeds said predetermined level.

4. The inspection apparatus according to claim 3 wherein said indicating means includes a display means for displaying the value of said overall distortion signal and said reference distortion signal.

5. The inspection apparatus according to claim 3 wherein said indicating means includes an alarm which is activated when the amount of overall distortion exceeds said predetermined level.

6. In a glass heat treating system including means for conveying individual sheets of glass through a heat treating tempering operation along a path, an inspection apparatus for detecting surface distortion in the individual glass sheet subsequent to the tempering operation, said inspection apparatus comprising:
a light source mounted to direct a first beam of light having a predetermined width toward one surface of the moving sheet at an oblique angle of incidence to cause a second beam of light to be reflected therefrom;
light detector means mounted to receive a plurality of light pattern produced by the second beam of reflected light for generating a plurality of output signals, each of said output signals representing the width of a respective one of said light patterns, each of said light patterns having a width which is a function of both the width of the first beam and the surface distortion of a separate inspected portion of the surface from which the second beam is reflected;
means responsive to the detector output signals for generating an overall distortion signal representing the amount of surface distortion in the sheet;
means for storing a predetermined reference distortion signal defining a predetermined level of surface distortion; and
means responsive to the overall distortion signal and the reference distortion signal for indicating when the amount of overall distortion exceeds said predetermined level.

7. The inspection apparatus according to claim 6 wherein said indicating means includes a display means for displaying the value of the overall distortion signal and the reference distortion signal.

8. The inspection apparatus according to claim 6 wherein said indicating means includes an alarm which is activated when the amount of overall distortion exceeds said predetermined level.

9. The inspection apparatus according to claim 6 including heat control means responsive to the overall distortion signal for controlling the temperature of the glass heat treating operation.

10. A method of detecting surface distortion in a sheet of reflective material comprising the steps of:
(a) directing a first beam of light having a predetermined width toward one surface of the sheet at an oblique angle of incidence to cause a second beam of light to be reflected therefrom;
(b) receiving a light pattern produced by the second reflected beam, said light pattern having a width which is a function of both the width of the first beam and the surface distortion of the portion of the surface from which the second beam is reflected;
(c) generating an output signal having a level representing the width of said light pattern; and
(d) generating an actual distortion signal in response to the output signal, the actual distortion signal representing the amount of surface distortion in the inspected portion of the sheet.

* * * * *